US005598260A

United States Patent [19]
Brewer et al.

[11] Patent Number: 5,598,260
[45] Date of Patent: Jan. 28, 1997

[54] APPARATUS AND METHOD FOR OPTICAL-BASED FLUX MONITORING OF AN EFFUSION CELL ADJACENT THE OUTPUT ORIFICE

[75] Inventors: Peter D. Brewer; Gregory L. Olson, both of Westlake Village, Calif.

[73] Assignee: Hughes Aircraft Company, Los Angeles, Calif.

[21] Appl. No.: 483,680

[22] Filed: Jun. 7, 1995

[51] Int. Cl.⁶ .................................................... G01N 21/31
[52] U.S. Cl. .............................. 356/72; 117/85; 117/86; 117/202
[58] Field of Search ............................. 356/72; 117/85, 117/86, 201, 202

[56] References Cited

U.S. PATENT DOCUMENTS 4,381,894   5/1983   Gogol, Jr. et al. ....................... 356/72

OTHER PUBLICATIONS

S. A. Chalmers and K. P. Killeen, "Real-Time Control of Molecular Beam Epitaxy by Optical-Based Flux Monitoring," App. Phys. Lett., vol. 63, No. 23, Dec., 1993, pp. 3131–3133.

Chih-shun Lu, "Atomic Absorption Spectroscopy for Deposition Rate Monitoring," excerpt, Handbook of Thin Film Process Technology, Inst. of Phys. Pub., Bristol and Phil., 1995.

Primary Examiner—Vincent P. McGraw
Attorney, Agent, or Firm—V. D. Duraiswamy; W. K. Denson-Low

[57] ABSTRACT

An apparatus and method for optically monitoring the output of an effusion cell during the MBE process where resonant radiation is guided through an optical radiation guide across the output orifice of the effusion cell to determine the atomic flux according to the concentration and absorbance of the resonant radiation at the output orifice of the effusion cell.

19 Claims, 2 Drawing Sheets

APPARATUS AND METHOD FOR OPTICAL-BASED FLUX MONITORING OF AN EFFUSION CELL ADJACENT THE OUTPUT ORIFICE

BACKGROUND OF THE INVENTION

1. Field of the Invention

The present invention relates in general to the use of molecular beam epitaxy (MBE) formation of semiconductor layers. More particularly, the present invention relates to an improved method of monitoring the atomic flux from an effusion cell during MBE.

2. Description of the Related Art

MBE is a versatile technique for depositing single crystal semiconducting, insulating, and metallic materials used in fabricating state-of-the-art electronic and opto-electronic devices. The advantages of MBE over other growth techniques include the ability to produce high purity materials with controlled composition, layer thickness, dopant concentrations, and structure. MBE growth is achieved by directing the output of effusion cells onto a heated substrate in an ultra-high vacuum chamber. The effusion cell's output consists of atoms and molecules of the desired growth and doping constituents to be deposited.

Practitioners of MBE have long sought real-time control of the growth rates and composition of the deposited material. Although MBE offers the potential for growth of device structures with atomic layer precision, current "dead-reckoning" methods employed for controlling the effusion cell fluxes place limitations on the extent to which the desired composition, thickness and layer uniformity can be achieved. Real-time monitoring and control of these parameters hold the keys to achieving higher accuracy in attaining target growth structures and improved run-to-run reproducibility. Current generation MBE machines rely on pre-growth calibrations such as ion gauge flux measurements or RHEED oscillations to determine proper flux conditions. These methods are time-consuming, provide no real-time feedback, and are only marginally accurate when growing demanding structures. These problems add directly to device manufacturing costs.

A superior technique for in situ measurement of the flux of atomic species from an MBE effusion cell is known as optical flux monitoring (OFM). OFM detects changes in transmitted light intensity due to absorption by the atoms emitted from an MBE effusion cell. The technique has been employed in MBE to measure the flux of aluminum (Al), gallium (Ga), and indium (In) in real-time. Investigators at Sandia National Laboratories (SNL) have used OFM in a feedback-controlled system for growth of AlAs/GaAs quarterwave layers for distributed Bragg reflectors, as described in "Real-time Control of Molecular Beam Epitaxy by Optical-Based Flux Monitoring," by S. A. Chalmers and K. P. Killeen, in App. Phy. Lett. 63, 3131 (1993).

In the OFM technique developed at SNL, a feedback-stabilized hollow cathode lamp is used as a light source. The resonant radiation generated by the hollow cathode lamp is focused with a quartz lens onto the end of a sending fiber optic cable where it is divided into a reference beam and a signal beam. The signal beam is passed through the atomic beam to be measured. The signal beam enters the MBE chamber through heated optical ports (to prevent deposition of material on the window) and is directed parallel to, and a few centimeters above the surface of the substrate, to measure the flux of atoms reaching the substrate. After the signal beam exits the chamber, it is re-focused onto a second receiving fiber optic cable where it is measured by a detector. A separate detector measures the reference beam, and a computer calculates the flux level based on the ratio of the signal beam to the reference beam.

Another commercial OFM product, "ATOMICAS", manufactured by Intelligent Sensor Technology, Inc., was developed to eliminate problems due to transmission changes in the OFM optical system that are not due to flux changes of the atomic beam. This problem causes baseline instability that has plagued earlier attempts of MBE flux monitors that failed to use heated optical ports. In the "ATOMICAS" approach, optical radiation from a second source that is not absorbed by the atomic beam is passed through the signal and reference optical paths. The second optical radiation source consists of a xenon flash lamp with a broadband spectral output overlapping the spectral region of the emission from hollow cathode lamp. With this second radiation, the transmission changes of the OFM optical system are monitored in real-time. This information is used to calibrate the atomic flux measurements.

The above-described OFM techniques have several disadvantages. In both techniques, the atomic flux is measured near the substrate surface. This geometry is not optimal for several reasons. The foremost problem is that the transmitted light intensity is affected by atoms reflected or desorbed from the substrate surface. Monitoring of the atomic flux at close proximity to the substrate allows double counting of atoms if they have non-unity sticking coefficients. Also, the atomic flux is not monitored continuously. In the existing OFM approaches, there is no signal when the effusion cell shutter is closed. This necessitates "dead-reckoning" based upon effusion cell temperature data to infer initial flux conditions after the shutter is opened. An additional shortcoming of the existing OFM detection geometry is that, due to the divergent nature of the effusive source, the OFM signal is measured just above the substrate, where the number of atoms crossing the optical path is lowest. Finally, implementing OFM on existing MBE machines with the current geometry requires substantial re-working of the vacuum chamber and cryo-panels.

SUMMARY OF THE INVENTION

In the present invention, these problems are eliminated by using quartz light guides on each effusion cell to allow the detection geometry to be at the output orifice of the effusion cell. This geometry minimizes the contribution of reflected atoms from the OFM signals, maximizes the signal strength of the absorption by the atomic flux, allows continuous monitoring of the beam flux, and is easily retrofitted onto existing MBE machines. The present invention provides a quantitative measurement of the flux of atoms emitted from an effusion cell during MBE. In accordance with the preferred embodiment of the present invention, the novel measurement system results in the ability to more accurately measure and control the flux of atoms from effusion cells. Accurate control and measurement is essential for reproducible MBE growth of semiconductor alloys and superlattice structures.

In the preferred embodiment of the present invention, the measurement of the atomic flux of an effusion cell is determined by taking the ratio of the intensities of two optical radiation measurements: (1) a measurement of optical radiation that passes through a signal optical path at the output orifice of the effusion cell (measuring absorption by the atomic beam) and (2) a measurement of optical radiation passing through a reference optical path external to the MBE chamber. The signal optical path is constructed with sending and receiving radiation guides that channel the light into and out of the MBE chamber through the effusion cell's mounting flange. At the output orifice of the effusion cell, a collimating lens at the output side of the sending radiation guide directs the signal optical path through the atomic beam. A collecting lens positioned across the output orifice opposite the collimating lens collects and focuses the optical radiation into the receiving radiation guide. The reference optical path consists of a length of fiber optical cable with appropriate optics to transmit the optical radiation through the cable and image it onto a detector.

The atomic flux from the effusion cell is determined by the ratio between the intensity of the resonant optical radiation that passes through the signal optical path and the intensity of the resonant optical radiation that passes through the reference optical path. The optical radiation launched through the signal and reference optical paths consists of both radiation that is strongly absorbed by the atomic species (resonant radiation) and that which is not absorbed (non-resonant radiation). The non-resonant radiation measures the transmission of the OFM optical system in real-time to provide an updated transmitted radiation intensity value used in the atomic flux calculation. The ratio of the intensities of the resonant optical radiations that pass through the signal optical path and the reference optical path is used to determine the flux of the atomic beam. The atomic flux from the effusion cell is determined using a modified Beer's law relationship between the concentration and absorbance of the resonant radiation by the atomic beam, that takes into account the velocity of the emitted atoms. Control of the atomic beam is accomplished by using the measured atomic flux as a primary input to the temperature controller for the effusion cell.

Because the present invention measures the atomic flux at the output orifice of the effusion cell, it has several advantages over existing OFM approaches. For example, the atomic flux is measured more accurately because the signal beam is not affected by atoms reflected or deabsorbed by the substrate. Existing OFM approaches may "count" atoms with a non-unity sticking coefficient twice because of the close proximity of the signal beam to the substrate where the atoms are reflected. This can produce a large error in the flux calibration. The problem can be especially severe if the sticking coefficient changes during the growth process.

The present invention can also continuously monitor the atomic flux even when the effusion cell shutter is closed. In the existing OFM approach, there is no signal when the shutter is closed. Initial flux conditions must be "dead-reckoned" estimated based on the effusion cell temperature. With the present invention, the atomic flux is continuously monitored so the flux condition is known when the shutter is open and the deposition process begins.

The present invention can also provide a greater signal-to-noise ratio than existing OFM approaches due to the measurement of the atomic beam being made at the output orifice of the effusion cell rather than the substrate surface. The number of atoms within the optical path at the output orifice is greater than the number across the substrate due to the divergent nature of the atomic beam. Consequently, the absorbance at the output orifice is greater, resulting in an improved signal-to-noise ratio at the output orifice. The present invention can also be retrofitted onto existing MBE devices without changes in the design of the MBE chamber. The optical-based flux monitor of the present invention can be configured so that it can be directly bolted onto existing MBE systems.

The present invention provides each effusion cell with its own monitoring system which measures the atomic flux in a continuous manner and minimizes the contribution of species with non-unity sticking coefficients. Continuous monitoring of the flux condition can therefore be achieved independent of the shutter position. This allows real-time control of the output flux from an individual effusion cell under all operating conditions.

DETAILED DESCRIPTION OF THE PRESENTLY PREFERRED EMBODIMENTS

Figure 1:
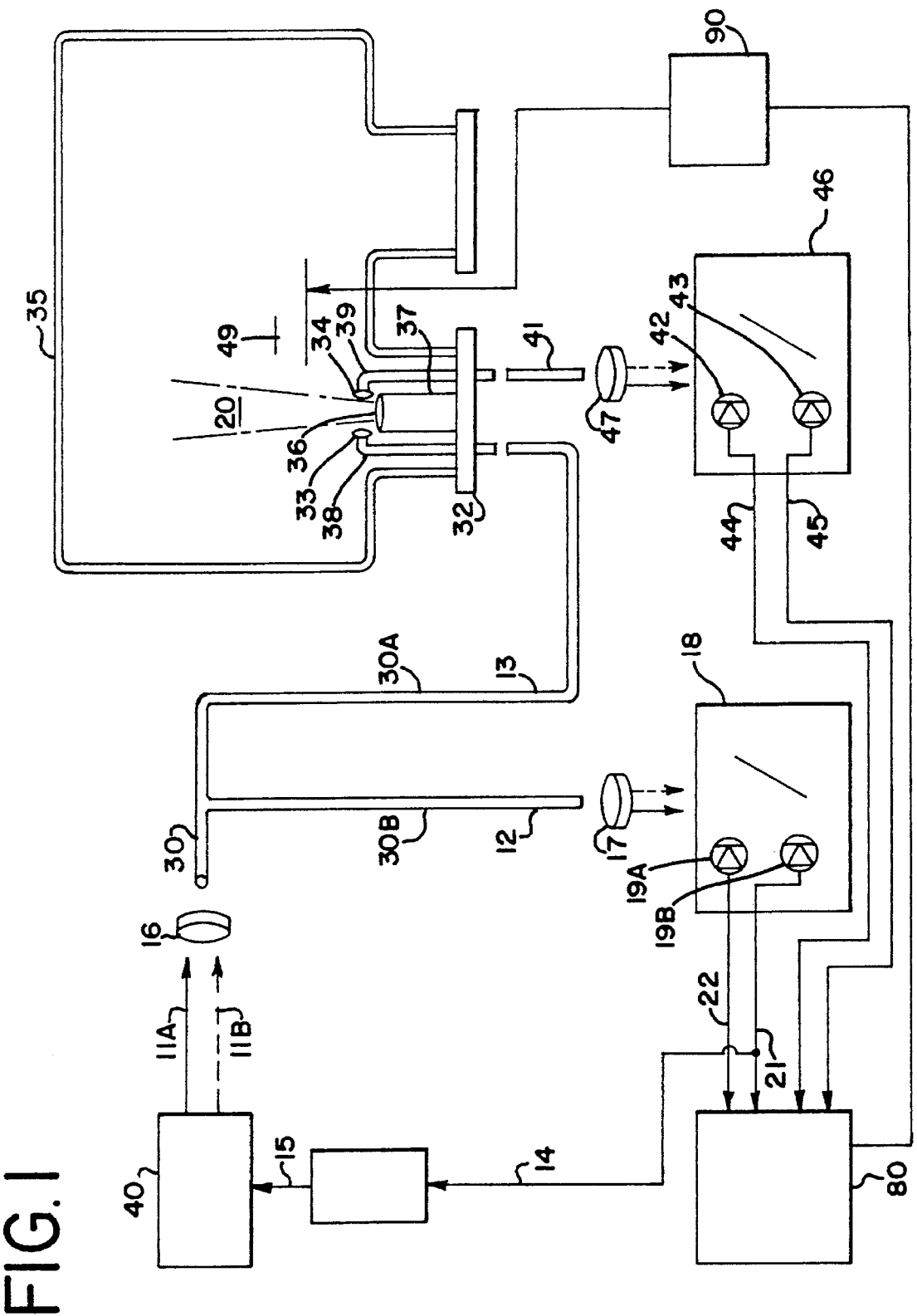
FIG. 1 is a schematic diagram of an optical flux monitoring system embodying the present invention.

The present invention is a novel method and system for making quantitative measurements of the flux of atoms emitted from an effusion cell during MBE as seen in FIG. 1. The preferred embodiment of the invention features a feedback-stabilized hollow cathode (HCL) or electrodeless discharge (EDL) lamp 40 which generates the resonant and non-resonant optical radiation 11A, 11B with respect to electronic transitions originating from the ground electronic state of the atomic species of interest. The non-resonant radiation is chosen to be close in wavelength to the resonant light. It is well known to users of HCL and EDL lamps that, for every available element, there are numerous choices of non-resonant emission sources. Commercial optical radiation sources of HCL and EDL include the elements Li, Be, B, Na, Mg, Al, Si, K, Ca, Sc, Ti, V, Cr, Mn, Fe, Co, Ni, Cu, Zn, Ba, Ge, As, Se, Rb, Sr, Y, Zr, Nb, Mo, Ru, Rh, Pd, Ag, Cd, In, Sn, Sb, Te, Cs, Ba, La, Hf, Ta, W, Re, Os, Ir, Pt, Au, Hg, Tl, Pb, Bi, Pr, Nd, Sm, Eu, Gd, Tb, Dy, Ho, Er, Tm, Yb, and Lu, where bold symbols represent elements currently used in MBE. A partial list of lamp suppliers include the Hamamatsu and Perkin Elmer Corporations. Lasers emitting radiation at the desired frequencies may also be used as a radiation source.

The accuracy of the measurement of MBE growth rates by in situ monitors is generally recognized by the MBE community to be within 1–5 percent. For elements having low absorption cross sections or are that are needed at extremely low flux levels, the light passing through the signal 13 and reference 12 optical paths must be measured with an accuracy of about 0.01 percent. Feedback control of lamp 40 is therefore necessary to stabilize the lamp output 11A, 11B. A portion of the light output of the lamp is used as a stabilization signal 15 to control of the lamp intensity. The feedback-stabilization technique reduces the lamp intensity variations to less than 0.1 percent. When combined with other stabilization techniques, such as two-beam referencing, the required stability and accuracy is achieved.

The stabilized resonant 11A and non-resonant 11B optical radiations are launched through a collecting lens 16 into the common end of a bifurcated, UV fiber optical cable 30. The two opposing ends of the cable lead to the reference optical path 12 and the signal optical path 13. Bifurcated UV fiber optical cables are commercially supplied by a number of vendors including American Fiber Optics, Inc.

The resonant and non-resonant optical signals 11A, 11B transmitted through the reference fiber optic cable 30 are imaged by a lens 17 onto the slits of a monochromator 18 that is used to spatially decouple the two signals. Separate detectors 19A, 19B housed in the monochromator measure the resonant 11A and non-resonant 11B optical signals. A portion of the resonant radiation output 14 provides a signal 15 for feedback-stabilization of the lamp 40. The remaining resonant radiation portion 21 is used along with the non-resonant radiation 22 as the reference signal in the atomic beam flux calculation.

Figure 2:
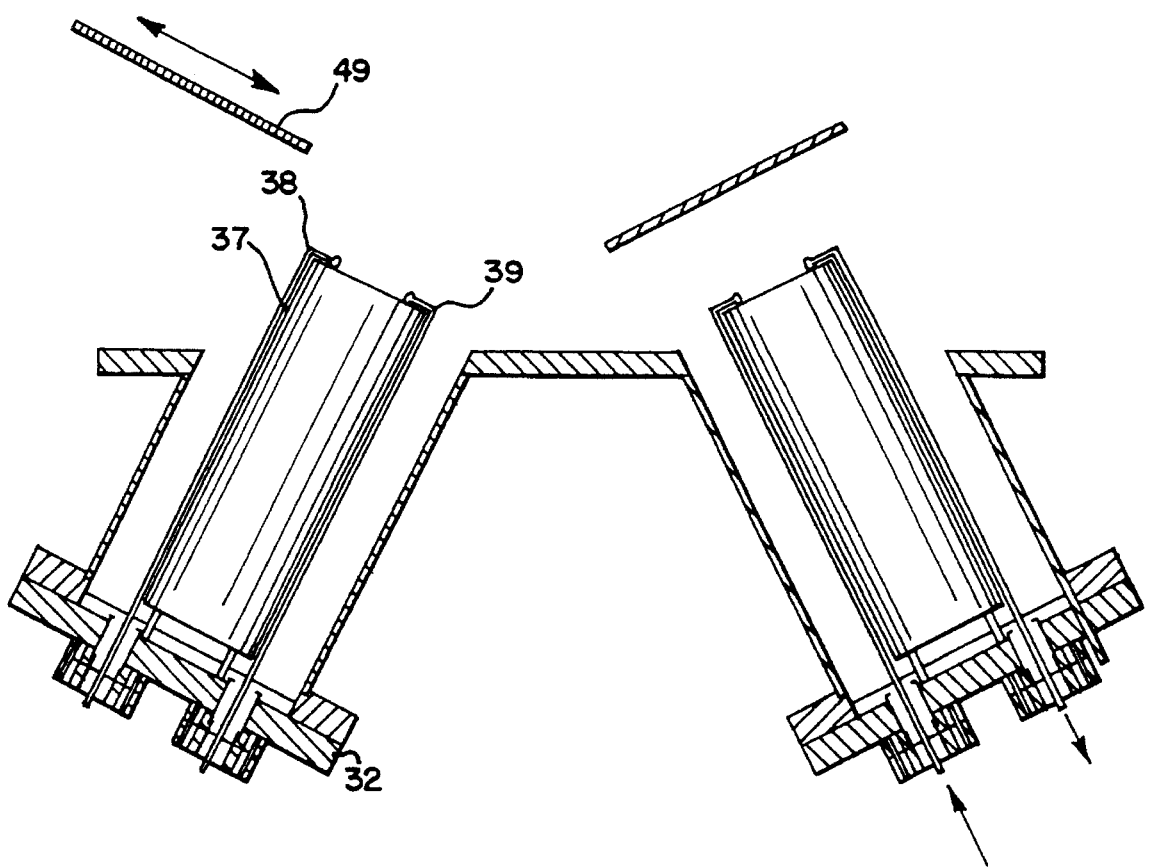
FIG. 2 illustrates a pair of effusion cells used in FIG. 1.

The second leg 30A of the bifurcated UV fiber optical cable directs the resonant and non-resonant optical radiation to the signal optical path. This signal path 13A passes through the atomic beam flux 20. The UV fiber optic cable 30A is physically coupled into the sending quartz optical radiation guide 38 that channels the signal path into the MBE chamber through the effusion cell's mounting flange 32. As shown by the pair of effusion cells depicted in FIG. 2, the MBE chamber 35 may be equipped with more than one effusion cell. Each effusion cell 37 can be provided with the flux monitoring system of the present invention.

Figure 2A:
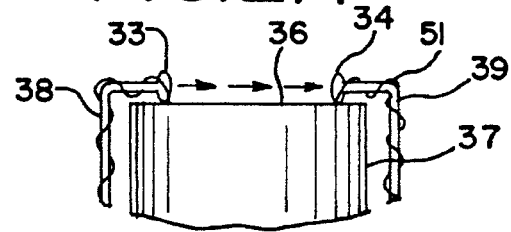
FIG. 2A illustrates an enlarged view of the output oriface of an effusion cell shown in FIG. 2.

A heated sapphire collimating lens 33 at the output side of the sending radiation guide directs the signal optical path 13A through the atomic beam 20 at the output orifice 36 of the effusion cell 37. As shown in FIG. 2A, the optical components residing inside the MBE chamber 35 are heated to prevent deposition of material on their optical surfaces. The optical components are heated by resistive heated filaments 51 in the vicinity of the quartz optical guides and sapphire lenses 33, 34. A heated sapphire collecting lens 34 positioned across the output orifice 36 opposite the collimating lens 33 collects and focuses the optical radiation into the receiving radiation guide 39. The receiving radiation guide 39 transmits the radiation out of the MBE chamber through the effusion cell's mounting flange 32 and into a sending UV fiber optical cable 41. The UV fiber optic cable directs the resonant and non-resonant radiation through a lens 47 and onto the slits of a monochromator 46 to spatially decouple the two signals. Detectors 42, 43 housed in the monochromator 46 measure the resonant and non-resonant optical signals.

In the preferred embodiment of the invention, Si photodiodes serve as detectors 42, 43. For applications requiring sensitivity which cannot be achieved by Si photodiodes, photomultiplier detectors may be used. Although a photomultiplier has greater gain characteristics than a Si detector, photomultipliers also exhibit greater drift and therefore require compensation techniques to offset drift effects.

The real-time transmission of the optical system is determined by a programmed computer using the following procedure. First, the ratio of the intensities of the non-resonant signal (NRS) and reference (NRR) beams is calculated. Second, a transmission normalizing constant ($C_{trans}$) is determined using initial system calibration measurements. Finally, the optical transmission of the system is calculated using the expression:

Transmission=$C_{trans}$ (NRS/NRR)

The atomic flux from the effusion cell is determined using a modified Beer's law relationship between the concentration and absorbance of the atomic beam. The atomic beam density (D) is related to the measured signal transmission (T) by Beer's law, which can be written as:

$$D=-C(v,S)\ln T, \quad (1)$$

where C(v,S) is a proportionality constant determined by the absorption cross-section, the temperature dependent sticking coeffieint, and the geometries of the atomic beam and the transmitted signal, and v is the atomic beam velocity. C(v,S) is a function of the velocity of because the absorption cross-section of the atomic beam is determined by the spectral overlap of the beam absorption profile and the lamp emission profile. The MBE growth rate ($r_g$) is the product of the beam density and the beam velocity:

$$r_g=vD=-vC(v,S)\ln T. \quad (2)$$

Because the beam velocity is determined by the effusion cell temperature, vC(v,S) is a unique function of the measured transmission. Therefore, vC(v,S) can be empirically determined by measuring the relationship between $r_g$ and T over the range of growth rates of interest. The empirically determined function vC(v,S) can then be inserted into the equation (2).

A general purpose computer 80 can be readily programmed by those skilled in the art to solve the above-described equations to determine the growth rate of materials deposited. The shutter 49 of the effusion cell is controlled 90 to the achieve the desired growth rate. Such a computer programmed can be readily developed by those skilled in the art.

Of course, it should be understood that a wide range of changes and modifications can be made to the preferred embodiment described above. It is therefore intended that the foregoing detailed description be regarded as illustrative rather than limiting and that it be understood that it is the following claims, including all equivalents, which are intended to define the scope of the invention.

We claim:

1. A device for monitoring the flux of atoms from an output orifice of an effusion cell during MBE comprising:

a radiation source generating a resonant radiation;

a first radiation guide mounted to direct the resonant radiation across the output orifice of the effusion cell; and a detector to detect the resonant radiation transmitted across the output orifice of the effusion cell adjacent the orifice.

2. The device of claim 1 where the radiation source is a feedback-stabilized hollow cathode lamp.

3. The device of claim 1 where the radiation source is an electrodeless-discharge cathode lamp.

4. The device of claim 1 where the radiation source is a laser.

5. The device of claim 1 where the first radiation guide is a fiber optic light guide.

6. The device of claim 1 where the detector is a Si photodiode.

7. The device of claim 1 where the detector is a photomultiplier.

8. The device of claim 1 where the first radiation guide is heated to prevent condensation of atoms emitted by the effusion cell.

9. The device of claim 1 further comprising:

a collimating lens to direct the resonant radiation from the first radiation guide across the output orifice; and a collecting lens to collect the resonant radiation transmitted across the output orifice by the collimating lens.

10. The device of claim 9 where the collimating and collecting lens are sapphire optics.

11. The device of claim 9 further comprising:

a second radiation guide to direct radiation collected by the collecting lens to the detector.

12. The device of claim 11 where the collimation and collecting lenses and second radiation guide are heated to prevent condensation of atoms emitted by the effusion cell.

13. The device of claim 1 further comprising: electronics to process the photodiode signals and provide shutter control signals to the effusion cell.

14. A device for monitoring the flux of atoms from an effusion cell during MBE comprising:

a feedback stabilized hollow cathode lamp generating an optical resonant radiation;

a first quartz light guide mounted to direct the optical resonant radiation across an output orifice of the effusion cell adjacent the orifice;

a detector to detect the optical resonant radiation transmitted across the output orifice of the effusion cell;

a sapphire collimating lens to direct the optical resonant radiation from the first radiation guide across the output orifice adjacent the orifice;

a sapphire collecting lens to collect the optical resonant radiation from the first radiation guide across the output orifice by the collimating lens; and electronics to process the detector signals and provide shutter control signals to the effusion cell.

15. The device of claim 14 where the electronics comprises a digital computer.

16. A method of monitoring the flux of atoms across an output orifice of an effusion cell during MBE comprising:

directing a radiation signal through the flux of atoms across the output orifice of the effusion cell adjacent the orifice;

measuring the change in the intensity of the radiation signal which is transmitted through the flux of atoms; and calculating the atomic flux based on the change of intensity of the radiation signal through the atomic flux.

17. The method of claim 16 where:

the radiation signal is an optical radiation signal.

18. The method of claim 16 where:

the measurement of the flux of atoms from the emission source is calculated using a modified Beer's law relationship between the concentration and absorbance of the flux of atoms and the signal beam which accounts for the velocity of the emitted particles.

19. The method of claim 16 further comprising:

controlling a shutter of the effusion cell using the calculated atomic flux signal.

* * * * *